United States Patent [19]

Salmond

[11] 4,042,596

[45] Aug. 16, 1977

[54] 2-ALKYL-5-PHENETHYL-4-OXAZOLECARBOXYLIC ACIDS AND DERIVATIVES

[75] Inventor: William G. Salmond, Mount Arlington, N.J.

[73] Assignee: Sandoz, Inc., E. Hanover, N.J.

[21] Appl. No.: 719,679

[22] Filed: Sept. 1, 1976

Related U.S. Application Data

[60] Division of Ser. No. 538,887, Jan. 6, 1975, Pat. No. 3,994,915, which is a continuation of Ser. No. 267,899, June 30, 1972, abandoned.

[51] Int. Cl.$^2$ ............................................ C07D 263/32
[52] U.S. Cl. .................................................. 260/307R
[58] Field of Search ..................................... 260/307 R

[56] References Cited

PUBLICATIONS

Elderfield – "Heterocyclic Compounds" – vol. 5 – John Wiley & Sons, Inc., New York (1957) – pp. 302–303.

*Primary Examiner*—Raymond V. Rush
*Attorney, Agent, or Firm*—Gerald D. Sharkin; Richard E. Vila; Frederick H. Weinfeldt

[57] ABSTRACT

2-Alkyl-5-phenethyl-4-oxazolecarboxylic acids, esters and carbonyl halides are disclosed, which are useful as intermediates in the preparation of known benzocycloheptaoxazoles.

7 Claims, No Drawings

2-ALKYL-5-PHENETHYL-4-OXAZOLECARBOXY-LIC ACIDS AND DERIVATIVES

This is a division of application of Ser. No. 538,887, filed Jan. 6, 1975 now U.S. Pat. No. 3,994,915, which in turn is a continuation of application Ser. No. 267,899, filed June 30, 1972, now abandoned.

This invention relates to the preparation of cyclic organic compounds, and more particularly to the preparation of certain benzocycloheptaoxazolones by a multi-step process, as well as novel intermediates in said process, and the preparation thereof.

The benzocycloheptaoxazolones obtained by this invention have the forumla (I)

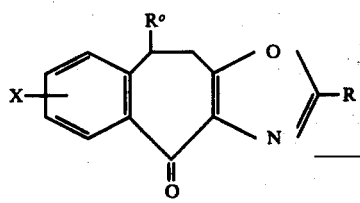

wherein
R represents lower alkyl, preferably containing from 1 to 4 carbon atoms, e.g., methyl, ethyl, propyl, isopropyl, and butyl;
R° represents hydrogen or phenyl; and
X represents hydrogen or halo, e.g. having an atomic weight of from about 18 to 80, e.g. fluoro, chloro or bromo; provided that when R° is phenyl, then X is a hydrogen atom.

The series of steps involved in the preparation of compounds I may be conveniently represented by Reaction Scheme A, below, wherein X, R° and R are as defined above, and R[1] is a lower alkyl, e.g. having from 1 to 6 carbon atoms, e.g. methyl, ethyl, propyl, butyl, amyl or hexyl, and is preferably unbranched, methyl and ethyl being particularly convenient, and R[2] is a lower akyl, e.g., having from 2 to 6 carbon atoms and, preferably unbranched, e.g. n-butyl, and Y is halo having an atomic weight of from about 34 to 128, i.e., chloro, bromo or iodo.

REACTION SCHEME A

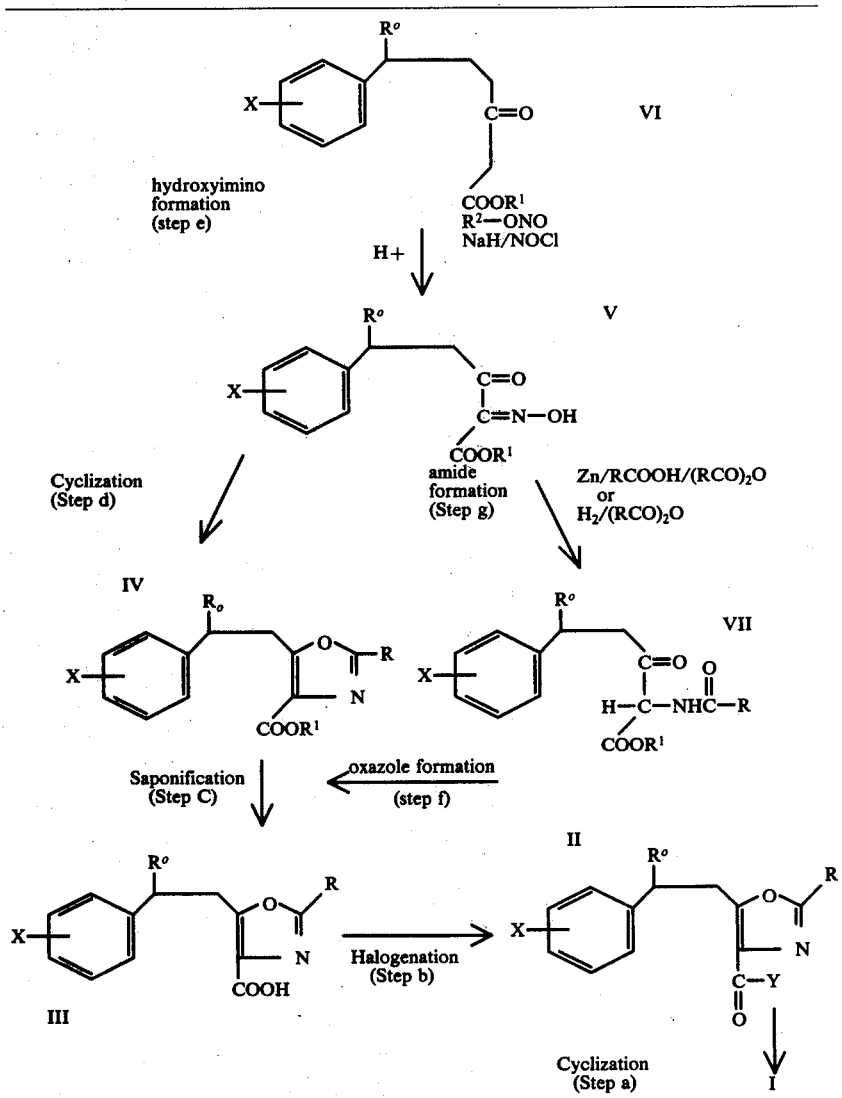

The cyclization of a compound II, i.e., an acyl halide of a 2-alkyl-5-phenethyl-4-oxazole-carboxylic acid to the corresponding compound I, i.e. step (a), may be carried out using as catalyst a Friedel-Crafts-type Lewis acid, e.g. a halide of boron, aluminum, zinc, tin or iron, preferably anhydrous aluminum trichloride, at from about 30° to 150° C., preferably at from about 30° to 100° C., in the presence of an inert solvent, such as carbon disulfide or 1,2 dichlorethane under essentially anhydrous conditions.

The halogenation of a compound III, i.e. of a 2-alkyl-5-phenethyl-4-oxazolecarboxylic acid, to obtain the corresponding acyl halide (a compound II) i.e., step (b) may be carried out in the conventional manner for converting a carboxylic acid to the corresponding acyl halide by treatment with a halogenating agent. The selection of the particular halogenating agent and conditions employed depends on what particular halide is desired as Y, i.e., chloro, bromo or iodo. Step (b), may be carried out with a suitable halogenating agent, e.g., thionyl chloride, thionyl bromide, phosphorus pentachloride and phosphorus pentabromide, in an organic solvent which is inert under the reaction conditions. e.g. chloroform or benzene, at a temperature from about 20° to the reflux temperature of the reaction mixture. An excess of the halogenating agent may, however, be used in place of the solvent if it is a liquid under the reaction conditions. The reaction product may be recovered by conventional means. Y is preferably chloro, and a preferred halogenating agent is thionyl chloride.

The saponification step (c) of a Compound IV to its free acid form (a Compound III) is suitably carried out in a conventional manner for the saponification of esters, e.g., in a mixture of water and water-miscible solvent, e.g. methanol or ethanol, or a cyclic ether, e.g. dioxane or tetrahydrofuran, with a strong inorganic base, preferably one that will yield a water soluble salt of the desired acid, e.g., sodium hydroxide or potassium hydroxide, at a temperature from 10° to 120° C., preferably at the reflux temperature of the solvent, e.g. at 80° to 100° C. The desired acid may be liberated from the salt thus obtained in conventional manner by treatment with an acid, e.g. acetic acid or hydrochloric acid.

The preparation of compound IV (step d), i.e. by cyclizing a suitable 2-hydroxyimino-substituted valerate (a compound V) may be carried out by treating a compound V with a carboxylic acid of the formula RCOOH (R being as defined above) and an anhydride of said acid in the presence of metallic zinc, preferably in finely divided form, e.g., zinc dust, e.g. at temperatures of from about 80° to 180° C., preferably at the reflux temperature of the reaction mixture, e.g. at about 140° C. An inert diluent or solvent, e.g., toluene or xylenes may be employed, but it is preferred where the carboxylic acid or its anhydride are liquid under the reaction conditions that such be employed in excess to serve as solvent or reaction medium. It is preferable to include a small portion of an alkaline metal salt of the carboxylic acid and mercuric chloride in the reaction mixture. Thus where R= methyl, a combination of sodium acetate, acetic acid, acetic anhydride, and mercuric chloride may advantageously be employed in step (d). The reaction is carried out for a period of from about 4 to 24 hours.

Alternatively, a compound IV may be prepared by a two step process from the corresponding compound V. First a compound V is treated in the same manner as in step (d), but for a shorter period of time, e.g. about ½ hour to 4 hours (step g) resulting in the formation of the corresponding compound VII, i.e. a lower alkyl ester of a 2-amido-3-oxo-5-phenylvalerate. The resulting compound VII may then be cyclized to the corresponding compound IV (step f), e.g. in the presence of a cyclo-dehydrating agent, such as thionyl -chloride or-bromide or an organic acid anhydride of the formula $(RCO)_2O$, e.g. acetic anhydride where R=methyl, at about 15° to 150° C., preferably at about the reflux temperature of the reaction medium. The reaction may be carried out in the presence of an inert solvent, e.g., benzene, toluene or xylene, however, where the cyclo-dehydrating agent is a liquid under the reaction conditions, it is preferred to employ such in excess to serve as solvent or reaction medium.

If desired, step (g) may be achieved to obtain a compound VII by treating a compound V with hydrogen gas in the presence of a hydrogenating catalyst such as one conventionally employed in the reductive acylation of oximes, e.g. palladium on charcoal or Raney nickel and in the presence of an appropriate organic acid anhydride, i.e. $(RCO)_2O$. The organic acid anhydride may serve in excess as reaction medium or solvent under the reaction conditions and such is preferred. However, an inert hydrocarbon diluent or solvent may be employed e.g. cyclohexane. The reaction is carried out at moderate temperatures, e.g. at 20° to 30° C., external heating not being required, and at moderate pressures, e.g., at from about 1 to 10 atmospheres of pressure, preferably at about 2.5 to 3.5 atmospheres. Where such catalytic reductive acylation is employed, the solid catalyst may be removed by filtration leaving the resulting compound VII and the organic acid anhydride, which mixture may serve for carrying out step (f), described above.

Compounds V are obtainable by treatment of a suitable 3-oxo-5-phenylvalerate ester, i.e. a compound VI, in a conventional manner for introducing a hydroxyimino group alpha to a carbonyl function, e.g. by reaction with a lower alkyl nitrite of the formmula $R^2ONO$, ($R^2$ being as defined above) under acidic conditions. The reaction may be carried out in an inert solvent, e.g. a lower alkanol, such a ethanol, at moderate temperatures, e.g. from about 10° to 50° C., preferably at about 20° to 30° C. The acidic conditions are conveniently provided by concentrated hydrochloric acid.

Step (e) may alternatively be carried out by treating a compound VI with sodium hydride and nitrosyl chloride in an inert diluent or solvent, e.g. a cyclic ether such as tetrahydrofuran or dioxane, at moderate temperatures, e.g. from 0° to 35° C., preferably at from 20° to 30° C., and under essentially anhydrous conditions.

Compounds VI are known and may be prepared as described in the literature, or where not known, may be prepared in the manner analogous to that for preparing known compounds.

Compounds I are useful as intermediates in the preparation of pharmaceutically useful compounds as disclosed in U.S. Pat. No. 3,598,835 (issued Aug. 10, 1971), and Belgian Pat. No. 745,016 (July 27, 1970) and are also useful per se as anti-inflammatories as described in said United States patent.

The following Examples are illustrative of the invention, and are in no way intended as limiting the scope of the invention. Temperatures given in the examples are Centigrade, and room temperature is 20° to 30° C., unless indicated otherwise.

EXAMPLE 1

2-Methyl-9,10-dihydro-4H-benzo[5,6]cyclohepta[1,2-d]oxazol-4-one

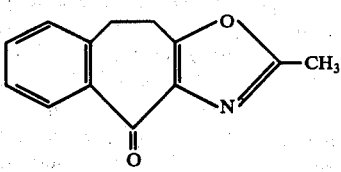

STEP A

Ethyl-2-hydroxyimino-3-oxo-5-phenylvalerate

To a solution of 22.0 g. of ethyl 3-oxo-5-phenylvalerate in 100 ml. of ethanol is added 40 ml. of 38% hydrochloric acid, and after 10 minutes 11.3 ml. of n-butyl nitrite is added thereto. The resulting mixture is allowed to stand at room temperature for 45 minutes, and then the ethanol portion is essentially removed under reduced pressure to obtain an oily residue. The residue is poured into about 500 ml. of water and extracted 3 times with 200 ml. of chloroform. The combined extracts are dried over anhydrous sodium sulfate, then evaporated to obtain the title compound as a residue.

STEP B

Ethyl 2-methyl-5-phenethyl-4-oxazole-carboxylate 27 g. of ethyl 2-hydroxyimino-2-oxo-5-phenylvalerate, 1.5 g. of sodium acetate, and 0.1 g. of mercuric chloride are dissolved in 150 ml. of acetic anhydride and 120 ml. of glacial acetic acid. 60 g. of zinc dust is added portion-wise over a period of 30 minutes, during which boiling occurs. The mixture is refluxed for 18 hours, and then cooled, filtered and evaporated to obtain a residue. The residue is dissolved in 200 ml. of chloroform and washed with 50 ml. of 10% aqueous sodium hydroxide, followed by 50 ml. of water. The chloroform solution was then dried over anhydrous sodium sulfate, and then evaporated under vacuum to obtain the title compound as an oil, which is suitable for use in the following step (Step C). The oil may be further refined, if desired, by vacuum distillation (b.p. 140° C. at 0.1 mm. of Hg).

STEP C 2-methyl-5-phenethyl-4-oxazolecarboxylic acid

To a solution of 4.0 g. of sodium hydroxide in 200 ml. of ethanol is added 27 l g. of ethyl 2-methyl-5-phenethyl-4-oxazolecarboxylate and the mixture boiled for 30 minutes. The mixture is cooled, and evaporated (under vacuum) to obtain crude sodium salt of the title compound as a solid residue which is washed with 25 ml. of ether. The residue is then dissolved in water, 8 ml. of glacial acetic acid added thereto and the mixture then extracted twice with 100 ml. portions of chloroform. The extract solutions are combined and then dried over anhydrous sodium sulfate and the solvent removed to obtain the title compound as a crystalline residue, which upon recrystallization from acetone ether (1:1) has a melting point of 128° to 130° C.

STEP D 2-methyl-5-phenethyl-4-oxazolecarbonyl chloride 2.5 g. of 3-methyl-5-phenethyl-4-oxazolecarboxylic acid is dissolved in 20 ml. of thionyl chloride and 20 ml. benzene, and the mixture refluxed for 2 hours. After cooling the mixture is evaporated to obtain the title acyl chloride as an oily residue, which may be used, without further refining, in Step E. Refining by chromatographing the thus obtained crude acid chloride in methylene chloride through a silica gel column and crystallization from acetone at low temperature (0°) yields refined title product, m.p. 38° to 39° C.

STEP E 2-methyl-9,10-dihydro-4H-benzo[5,6]cyclohepta[1,2-d]oxazol-4-one 1.0 of 2-methyl-5-phenethyl-4-oxazolecarbonyl chloride (obtainable by Step D, above) in 15 ml. of carbon disulfide, 2.5 g. of anhydrous aluminum chloride added, and the mixture refluxed for 1 hour. The mixture is then cooled, poured on to ice, and extracted twice with 10 ml. portions of chloroform. The extracts are combined, dried over anhydrous sodium sulfate and evaporated (under vacuum) to obtain a solid residue, which is recyrstallized from ethyl acetate to obtain the title compound, m.p. 174°–176°.

Using an equivalent amount of (a) ethyl 3-oxo-5-(o-chlorophenyl)-valerate or (b) ethyl 3-oxo-5,5-diphenylvalerate in place of the ethyl 3-oxo-5-phenylvalerate, used in Step A of this example, and repeating the procedures described in Steps B, C, D and E, there is similarly obtained (a) 8-chloro-2-methyl-9,10-dihydro-4H-benzo[5,6]cyclohepta[1,2-d]oxazol-4-one or (b) 2-methyl-9-phenyl-9,10-dihydro-4H-benzo[5,6]cyclohepta[1,2-d]oxyzol-4-one.

EXAMPLE 2

2-methyl-9,10-dihydro-4H-benzo[5,6]cyclohepta-[1,2-d]oxazol-4-one 1.0g. of 2-methyl-5-phenethyl-4-oxazolecarboxylic acid(obtainable by Step C of Example 1) is added to 8 ml. of thionyl chloride, and the mixture refluxed for 20 minutes. The reaction mixture is then evaporated to obtain a residue (the acyl chloride) which is then dissolved in 15 ml. of carbon disulfide, and 2.5 g. of anhydrous aluminum trichloride added thereto. The mixture is refluxed for 1 hour and the title product then recovered as described in Step E of Example 1.

EXAMPLE 3

Ethyl 2-methyl-5-phenethyl-4-oxazolecarboxylate

STEP A

Ethyl 2-acetamido-3-oxo-5-phenylvalerate

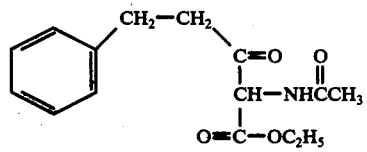

12 g. of ethyl-2-hydroxyimino-3-oxo-5-phenethylvalerate is added to a mixture of 48 g. of glacial acetic acid, 36 g. of acetic anhydride, 0.6 g. of sodium acetate, and 0.06 g. of mercuric chloride. 24 g. of zinc dust is then added to the mixture over a period of 30 minutes during which the mixture begins to boil. The mixture is then refluxed for 40 minutes, then cooled and filtered. The filtrate is evaporated (under vacuum) to obtain an oily residue consisting predominantly of ethyl 2-acetamido-3-oxo-5-phenylvalerate.

STEP B

Ethyl 2-methyl-5-phenethyl-4-oxazole-carboxylate

To the entire oily residue obtained in Step A is added at 0° C., 60 ml. of thionyl chloride and the resulting mixture refluxed for 40 minutes. The reaction mixture is then cooled and evaporated (under vacuum) to obtain a residue. The residue is dissolved in methylene chloride, and the solution washed with 5% aqueous sodium bicarbonate (100 ml.). The organic layer is then dried over anhydrous sodium sulfate and evaporated (under vacuum) to obtain the title compound as a crude residue.

EXAMPLE 4

Ethyl 2-methyl-5-phenethyl-4-oxazolecarboxylate 14.0 g. of ethyl 2-hydroxyimino-3-oxo-5-phenethylvalerate are dissolved in 300 ml. of acetic anhydride. To the solution is added 2.5 g. of 10% palladium on charcoal and the mixture kept under hydrogen at 3 atmospheres for 18 hours with agitation. The catalyst is then removed by filtration to obtain a solution essentially consisting of ethyl 2-acetamido-3-oxo-5-phenethylvalerate in acetic anhydride. This solution may be evaporated under vacuum, to obtain a residue, which upon recrystallization from ether yields refined ethyl 2-acetamido-3-oxo-5-phenylvalerate, m.p. 54°–55°.

If the solution of crude ethyl 2-acetamido-3-oxo-5-phenethylvalerate in acetic anydride is refluxed for 18 hours, ethyl 2-methyl-5-phenethyl-4-oxazolecarboxylate is obtained, which may be recovered as described in Example 3, Step B.

EXAMPLE 5

Ethyl 2-methyl-5-phenethyl-4-oxazole-carboxylate

STEP A

Ethyl 2-hydroxyimino-3-oxo-5-phenethylvalerate

A solution of 22 g. of ethyl 3-oxo-5-phenylvalerate in 50 ml. of tetrahydrofuran is added, dropwise, to a stirred suspension prepared from 4.3 g. of 57% sodium hydride dispersion in petroleum oil and 50 ml. tetrahydrofuran. After stirring 15 minutes at room temperature, 6.5 g. of nitrosyl chloride gas is passed into the stirred mixture. The resulting mixture is stirred for 1 hour and may be then used directly in Step B, below, as it consists essentially of ethyl 2-hydroxyimino 3-oxo-5-phenethylvalerate and sodium chloride in tetrahydrofuran.

STEP B

Ethyl 2-acetamido-3-oxo-5-phenethylvalerate

To the entire hydroxyimino-containing mixture obtained in Step A, above, is added 160 ml. of acetic acid, 110 ml. of glacial acetic acid, 1.8 g. of sodium acetate and 0.15 g. of mercuric chloride. Zinc dust (60 g.) is then added portion-wise with stirring. The reaction mixture is heated to boil off the tetrahydrofuran and then refluxed for 40 minutes. The reaction mixture is then cooled, and filtered, and the filtrate evaporated to obtain crude ethyl 2-acetamido-3-oxo-5-phenylvalerate which is suitable for use in Step C, below.

STEP C

Ethyl 2-methyl-5-phenethyl-4-oxazolecarboxylate 1 g. of ethyl 2-acetamido-3-oxo-5-phenylvalerate is dissolved in 4 ml. of thionyl chloride, and the solution heated for 15 minutes. The reaction mixture is then evaporated under vacuum to obtain a residue which is then washed with 10 ml. of 5% aqueous sodium bicarbonate solution, then extracted twice with 25 ml. of methylene chloride. The combined extracts are then evaporated under vacuum to obtain ethyl 2-methyl-5-phenethyl-4-oxazolecarboxylate as an oil.

What is claimed is:

1. A compound of the formula

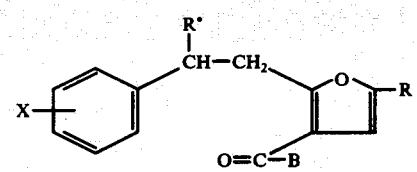

wherein
1 is either —OR¹, —OH or —Y,
R is alkyl having from 1 to 4 carbon atoms;
Y is chloro, bromo or iodo;
X is a hydrogen atom or fluoro, chloro or bromo;
R¹ is alkyl having from 1 to 6 carbon atoms;
R° is either a hydrogen atom or phenyl; provided that when R° is phenyl, then X is a hydrogen atom.
2. A compound of claim 1, wherein B is —OR¹.
3. The compound of claim 2 which is ethyl 2-methyl-5-phenethyl-4-oxazole-carboxylate.
4. A compound of claim 1 wherein B is —OH.
5. The compound of claim 4 which is 2-methyl-5-phenethyl-4-oxazolecarboxylic acid.
6. A compound of claim 1 wherein B is Y
7. The compound of claim 6 which is 2-methyl-5-phenethyl-4-oxazolecarbonyl chloride.

* * * * *

UNITED STATES PATENT AND TRADEMARK OFFICE
CERTIFICATE OF CORRECTION

PATENT NO. : 4,042,596
DATED : Aug. 16, 1977
INVENTOR(S) : William G. Salmond

It is certified that error appears in the above-identified patent and that said Letters Patent are hereby corrected as shown below:

Column 2, line 17, the word "akyl" should read -- alkyl --;

Column 4, line 39, the word "formmula" should read -- formula --;

Column 4, line 67, the word "centrigrade" should read -- centigrade --; Column 5, line 55, "27 1 g. of ethyl" should read -- 27 g. of ethyl --; Column 6, line 19, "1.0 of" should read -- 1.0 g. of --; Column 8, in Claim 1, in the structural formula, the right-hand cyclic structure should appear as -- 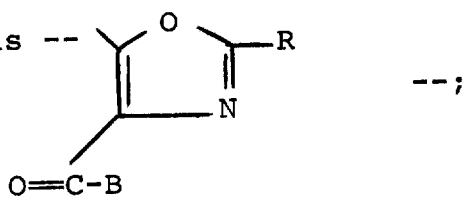 --;

Column 8, line 40, "1 is either" should read -- B is either --.

Signed and Sealed this

Eighth Day of August 1978

[SEAL]

Attest:

RUTH C. MASON
Attesting Officer

DONALD W. BANNER
Commissioner of Patents and Trademarks